(12) United States Patent
Patel et al.

(10) Patent No.: US 9,388,952 B2
(45) Date of Patent: Jul. 12, 2016

(54) HEAD-MOUNTABLE LIGHT DEVICE

(71) Applicants: Birju Patel, Middlesex (GB); Roni Stone, London (GB)

(72) Inventors: Birju Patel, Middlesex (GB); Roni Stone, London (GB)

( * ) Notice: Subject to any disclaimer, the term of this patent is extended or adjusted under 35 U.S.C. 154(b) by 0 days.

(21) Appl. No.: 14/418,173

(22) PCT Filed: Jul. 29, 2013

(86) PCT No.: PCT/IB2013/056233
§ 371 (c)(1),
(2) Date: Jan. 29, 2015

(87) PCT Pub. No.: WO2014/020527
PCT Pub. Date: Feb. 6, 2014

(65) Prior Publication Data
US 2015/0192259 A1    Jul. 9, 2015

(30) Foreign Application Priority Data

Jul. 29, 2012 (GB) ................................. 1213478.9

(51) Int. Cl.
| F21V 9/00 | (2015.01) |
| F21L 4/02 | (2006.01) |
| A61N 5/06 | (2006.01) |
| F21L 4/04 | (2006.01) |
| F21V 21/08 | (2006.01) |
| F21V 21/084 | (2006.01) |
| F21V 23/04 | (2006.01) |
| F21W 131/10 | (2006.01) |
| F21Y 101/02 | (2006.01) |

(52) U.S. Cl.
CPC ................. *F21L 4/02* (2013.01); *A61N 5/0618* (2013.01); *F21L 4/04* (2013.01); *F21L 15/14* (2013.01); *F21V 21/084* (2013.01); *A61N 2005/0648* (2013.01); *A61N 2005/0662* (2013.01); *F21V 23/0414* (2013.01); *F21V 23/0471* (2013.01); *F21W 2131/10* (2013.01); *F21Y 2101/02* (2013.01)

(58) Field of Classification Search
CPC ............... F21L 4/02; F21L 4/04; F21L 15/14; A61N 5/0618; A61N 2005/0648; A61N 2005/0662; F21V 21/084; F21V 23/0414; F21V 23/0471; F21W 2131/10; F21Y 2101/02
USPC .......................................................... 362/231
See application file for complete search history.

(56) References Cited

U.S. PATENT DOCUMENTS

| 2005/0237479 | A1 | 10/2005 | Rose | |
| 2007/0064413 | A1* | 3/2007 | Slater | A42B 1/244 362/106 |
| 2010/0217358 | A1 | 8/2010 | Hebert et al. | |
| 2010/0271810 | A1 | 10/2010 | Lau | |
| 2010/0313335 | A1* | 12/2010 | Waters | A42B 1/244 2/209.13 |

(Continued)

FOREIGN PATENT DOCUMENTS

| BE | 1018173 A3 | 6/2010 |
| CN | 201568753 U | 9/2010 |

(Continued)

*Primary Examiner* — Anh Mai
*Assistant Examiner* — Hana Featherly

(57) ABSTRACT

A head-mountable portable device comprising: a first light source configured to emit a beam of white light in a first direction; and a second light source configured to emit blue light, the second light source being configured such that the blue light is substantially emitted in a second direction that is different to the first direction.

17 Claims, 2 Drawing Sheets

(56) References Cited

U.S. PATENT DOCUMENTS

2011/0050123 A1 3/2011 Duerr et al.
2011/0130810 A1 6/2011 Gerardo

FOREIGN PATENT DOCUMENTS

| | | |
|---|---|---|
| CN | 201772277 U | 3/2011 |
| DE | 19518898 A1 | 11/1996 |
| JP | 2002350790 A | 12/2002 |
| RU | 2330693 C2 | 2/2008 |
| WO | 8908476 A1 | 9/1989 |
| WO | 2009023968 A1 | 2/2009 |
| WO | 2012006653 A1 | 1/2012 |
| WO | 2012040854 A1 | 4/2012 |

* cited by examiner

HEAD-MOUNTABLE LIGHT DEVICE

CROSS-REFERENCE TO RELATED APPLICATIONS

This application is an U.S. national phase application under 35 U.S.C. §371 based upon co-pending International Application No. PCT/IB2013/056233 filed on Jul. 29, 2013. Additionally, this U.S. national phase application claims the benefit of priority of co-pending International Application No. PCT/IB2013/056233 filed on Jul. 29, 2013 and Great Britain Application No. 1213478.9 filed on Jul. 29, 2012. The entire disclosures of the prior applications are incorporated herein by reference. The international application was published on Feb. 6, 2014 under Publication No. WO 2014/020527.

BACKGROUND OF THE INVENTION

1. Field of the Invention

This invention relates to a portable light emitting device that is mountable on the head of a user.

2. Description of the Prior Art

Portable electric lamps and more particularly head torches (also known as head lamps) can be utilised by a user to provide light while keeping their hands free. Head torches are commonly used on trekking expeditions, by climbers, explorers, miners, sailors, cavers, divers, rescue workers and others.

This invention seeks to solve some certain previously unrecognised problems with regards to the user of a head torch.

SUMMARY OF THE INVENTION

According to a first aspect of the disclosure, there is provided a head-mountable portable device comprising: a first light source configured to emit a beam of white light in a first direction; and a second light source configured to emit blue light.

Suitably, the second light source is configured such that the blue light is substantially emitted in a second direction that is different to the first direction.

Suitably, the first light source is configured such that direction of the beam of white light is adjustable independently of the second light source.

Suitably, the second light source is configured such that the direction that the blue light is substantially emitted is adjustable independently of the first light source.

Suitably, the second light source is configured so as to substantially emit the blue light towards the face or one or more eyes of a user.

Suitably, the light emission spectrum of the second light source is between 400 nm and 550 nm.

Suitably, the light emission spectrum of the second light source is between 420 nm and 500 nm.

Suitably, the light emission spectrum of the second light source is between 446 nm and 477 nm.

Suitably, the first light source is configured to emit light at a first luminous flux and the second light source is configured to emit light at a second luminous flux that is lower than the first luminous flux.

Suitably, the irradiance of the light emitted by the second light source is 0.0003 W cm$^{-2}$ at about 3 cm from the light source.

Suitably, the second light source is configured so as to emit the blue light in a beam that is broader than the beam of the white light.

Suitably, the second light source is configured such that the blue light emitted is substantially diffuse.

Suitably, the second light source comprises a diffuser.

Suitably, the diffuser comprises any one or more of: frosted glass; titanium oxide; plastic diffusers: lightguides; lens; film diffuser; sheet diffuser; or sandblasted coating.

Suitably, the device further comprises a strap configured so as to mount the device on a user's head.

Suitably, the device further comprises a control circuit configured to independently control the first and second light sources.

Suitably, the control circuit is configured to independently supply power to the first and second light sources.

Suitably, the control circuit is further configured to incrementally increase the power supply to the second light source over a predetermined amount of time from a first power level to a second power level, wherein the second power level causes the second light source to emit light at a predetermined luminous flux.

Suitably, the control circuit is further configured to incrementally decrease the power supply to the second light source over a second predetermined amount of time from the second power level to the first power level.

Suitably, the first power level is substantially zero or at a power level so as to not cause any substantial emission of light from the second light source.

Suitably, the device further comprises: a detector configured to measure the intensity of blue light, wherein the control circuit is further configured to adjust the power supplied to the second light source such that the power supplied is dependent on said measured intensity.

Suitably, the power supplied is dependent on a threshold intensity.

Suitably, the control circuit is configured to increase the power supplied to the second light source if the said measured intensity is lower than the threshold intensity.

Suitably, the control circuit is configured to decrease the power supplied to the second light source if the said measured intensity is higher than the threshold intensity.

Suitably, the second light source is configured such that the blue light is emitted in the first direction at a luminous flux that is substantially equal to or greater than the white light.

Suitably, the second light source comprises one or more LEDs or one or more OLEDs or one or more quantum-dot-LEDs or one or more ACELs or a combination thereof.

Suitably, the luminous flux of the blue component of the white light is lower than the luminous flux of the other components of the white light.

Suitably, the device further comprises a third light source configured to emit infrared light.

Suitably, comprising a speaker configured to emit sound.

According to a second aspect of the invention, there is provided a portable lamp comprising: a means for mounting the lamp on to a head; a first light source configured to emit light with a first emission spectra at a first luminous flux in a first direction; and a second light source configured to emit light with a second emission spectra at a second luminous flux in a second direction that is different to the first direction, wherein the second emission spectra is narrower than the first emission spectra and the first luminous flux is greater than the second luminous flux.

According to a third aspect of the invention, there is provided a method of stimulation for a human user of a head torch, the head torch comprising a white light source and a separate blue light source, the method comprising the step of: supplying the blue light to the eyes of the user.

BRIEF DESCRIPTION OF THE DRAWINGS

For a better understanding of the present invention, reference is made by way of example to the following drawings, in which.

DETAILED DESCRIPTION OF THE INVENTION

Figure 1:
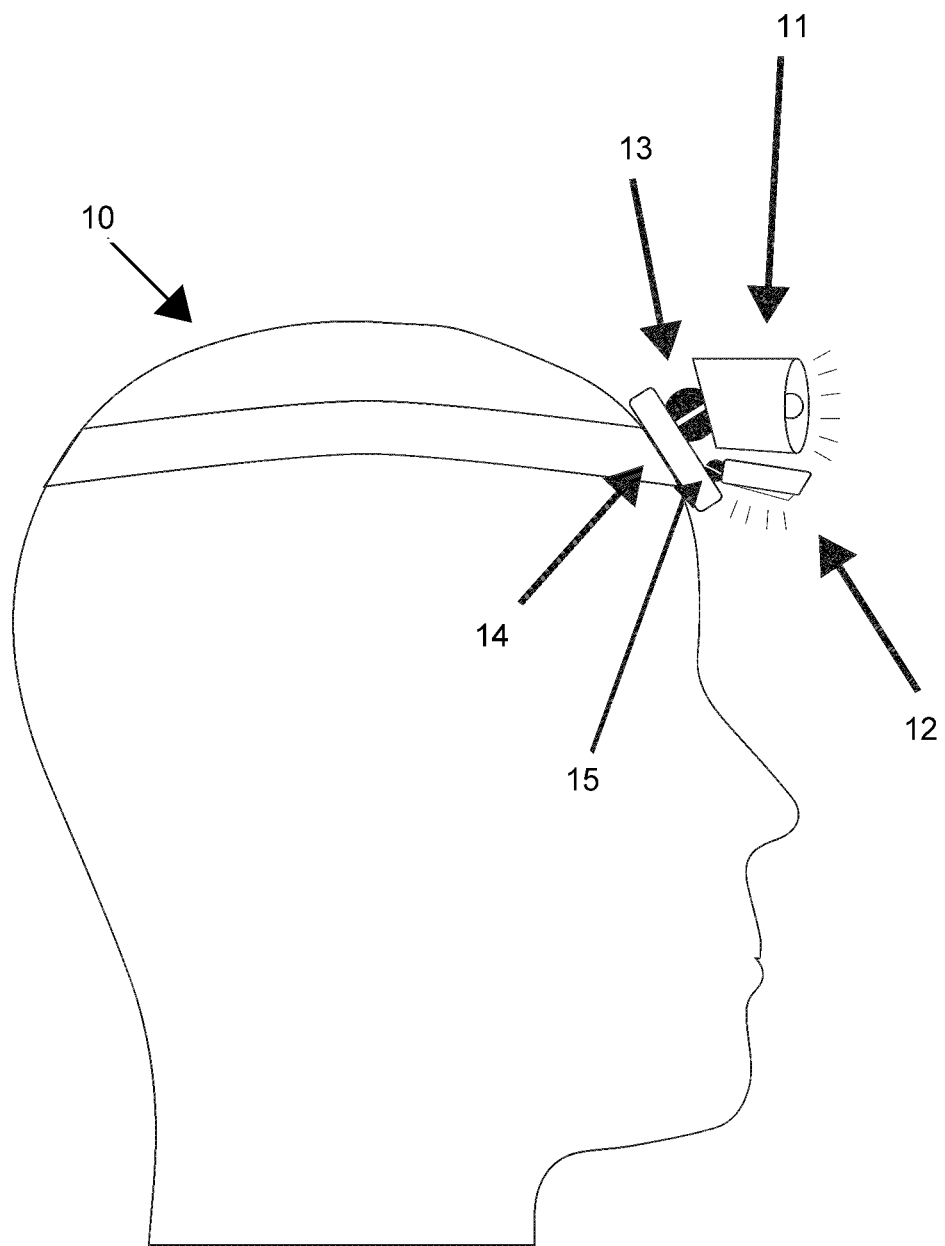
FIG. 1 shows an embodiment of a head torch.

Users may use the head torch at night and for prolonged periods. For example, many tourists climb various mountains at night so as to reach the summit to see the sunrise. Other users may use head torches during the day where there is no or little natural daylight, such as in mines or by deep-sea divers. In some cases, prolonged activity (mental and/or physical) may be required while using a head torch at times or in areas where there is no or very little natural daylight or other sources of artificial light. Working in conditions with low light may create problems for the user, such as the feeling of tiredness and/or sleepiness. The feeling of sleepiness may be enhanced under certain conditions, such as low temperatures, high altitude, low oxygen, abnormal sleeping patterns, shift-work and others. Such conditions can have an effect on the user's circadian rhythm, which can lead to the user feeling sleepy. Undergoing activities when the user's natural circadian rhythm dictates that the user should be sleeping can also lead to the user feeling sleepy. This can cause a lack of alertness, lower reaction times and reduce the cognitive abilities of the user. Such impairments in the user's abilities can be dangerous when undergoing certain risky activities such as mountain climbing, deep-sea diving, mining and others.

It is possible to reduce such risk by increasing the alertness and reducing the feeling of sleepiness of the user. This can be achieved by eating or drinking certain foodstuffs that include stimulants such caffeine. However, it may not be convenient to do so, or it may not be available, during certain activities such as deep-sea diving or in mines.

A head torch is conventionally used as a means of providing light to users so that they can be guided and see objects when undertaking activities such as those mentioned above. The inventors have invented a device that provides light so users can conveniently see things in the dark as well as providing a means to mitigate or lessen the feeling of tiredness or sleepiness for the user.

The present invention provides a device that comprises first light source that allows the user to see objects in low/no light conditions. The first light source can be configured so that the light from it is directed in front of the user, but not directed towards the eyes or face of the user. Preferably, the first light source is a white light source. The first light source may be adjustable so as to provide other colours, for example, a red light (which is sometimes used to reduce glare when light is directed towards the eyes of other people). The light from the first light source can be directed in front of the user such that the light from the first light source can only be received by the eyes of the user if that light has reflected off an object in front of the user.

The device also comprises a second light source for increasing the alertness and/or decreasing the feeling of tiredness or sleepiness of the user. This effect on the user is achieved by providing light of certain wavelengths that can help alter the amount of certain chemicals and hormones produced by the body of the user.

Scientific research has shown that the human body functions to the pace of an internal biological "clock". This clock, also known as the circadian rhythm or cycle, is located in the brain and is regulated by exposure to natural or artificial light. It has been found that humans tend to exhibit different degrees of alertness at different phases in their circadian cycle.

Activities, such as those mentioned above, can sometimes coincide with inappropriate points in the circadian cycle of a user, for example trekking at night. During these periods the human body produces melatonin which controls the circadian rhythm telling the human body that it is in the sleep part of the wake-sleep cycle. However, it in operation of a head lamp that the user may not wish to be in this part of the cycle. The present invention provides means to adjust or shift the user's circadian cycle to better correlate the cycle with the activities of the user.

Because one of the ways the circadian cycle is regulated is by light, exposure to light at specific wavelengths and intensities can effectively adjust the circadian phase. Exposure to specific wavelengths and intensities of light can lead to the body adjusting the amount of the light-sensitive hormone melatonin being released. This leads to a corresponding adjustment in the user's circadian rhythm and consequently causes a change in the alertness and level of sleepiness being felt by the user.

FIG. 1 shows an embodiment of the present invention. Head torch 10 comprises a first light source 11 and a second light source 12. The light sources can be attached to a single support 14. The support 14 can be attached to a means (for example, a strap) for mounting the head torch on to the head of a user (not shown in the figure). The first light source 11 comprises a light source that is capable of emitting white light. The first light source 11 may be a conventional light source that is used in conventional known head torches, such as those used for trekking. Such conventional head torches can also provide light of different colours, (e.g. red light, which helps preserve night vision) and can also be utilised in the first light source for the head torch of the present invention. The first light source 11 can function as a conventional torch that allows a user to see objects in low/no light conditions. As will be described later, the first light source 11 can also be an unconventional source of light that has an emission spectrum that acts to compensate for certain effects that the second light source 12 can cause.

The direction of the beam of light from the first light source 11 can be adjusted. The first light source 11 can be attached to an adjusting means, such as the pivot point 13 shown in FIG. 1. The pivot point 13 allows the position of the first light source 11 to be adjusted with respect to the other components of the head torch and/or the user wearing the head torch. The first light source 11 can pivot about the pivot point 13 from a first pivot end point to a second pivot end point. The pivot end points can define an arc within which the beam of light from the first light source can be directed. Preferably, when the head torch is worn by the user, the arc is in front of the user. One of the pivot end points can be arranged such that, when the head torch is worn by the user, the beam of light is unable to be directly directed into the face or eyes of the user.

The second light source 12 comprises a light source that is capable of emitting blue light. The second light source may emit a beam of blue light that can be directed. Preferably, the light emitted by the second light source is between 400 and 550 nm. Light with a wavelength of between 400 and 550 nm can have the effect of shifting the circadian cycle of a user, as discussed above. More preferably, the light emitted by the second light source is between 446 and 477 nm (and/or the light emitted by the second light source comprises light within this wavelength range). This more preferable range provides a more enhanced effect of shifting the circadian cycle of the user. Specific wavelengths in this range are more effective at causing the body to alter the amount of melatonin released. For example, light emissions peaking around 464-468 nm is particularly effective. Thus, in one embodiment, the second light source emits light that is centred around 464-468 nm. This leads to a faster and more noticeable response in the user of feeling more alert and less sleepy or more awake. The blue light is the key factor in controlling/suppressing melatonin production.

The second light source 12 can be positioned such that the light emitted by it is directed towards the user. Preferably, the light is directed towards the face of the user. More preferably, the light is directed towards one or both eyes of the user.

Preferably, the light emitted from the second light source 12 is substantially directed in a direction (e.g. towards the user's face/eyes) that is different to the direction that the light from the first light source is emitted (e.g. in front of the user).

The positioning of the second light source can be adjusted so that the light emitted by it can be directed towards the face and/or eyes of the user. The direction at which the light from the second light source is emitted may be adjusted by a number of appropriate adjusting means. Each user may wear the head torch at different positions on their head relative to their eyes, thus an adjusting means allows the user to ensure that the light emitted by the second light source can be directed towards their eyes. One example of an adjusting means is shown in FIG. 1 at 15. The adjusting means 15 can be rotated to any position within a first position and a second position. Rotation of the adjusting means causes the direction at which the light is substantially emitted to be adjusted accordingly.

Figure 2:
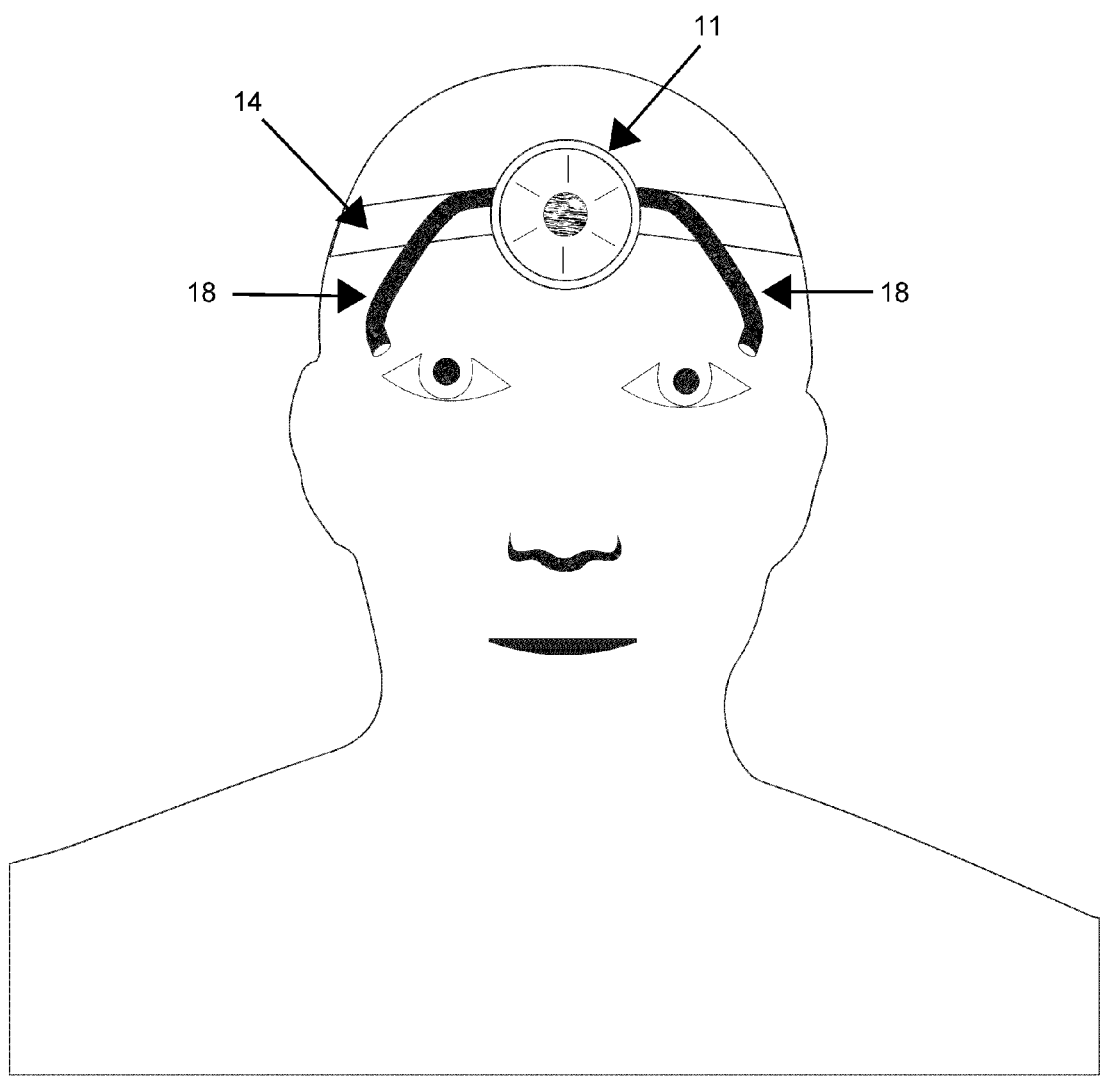
FIG. 2 shows another embodiment of a head torch.

Appropriate adjusting means may be employed that allows the direction of the light from the second light to be adjusted according to the user's eyes and/or face and their preferred location of wearing the head torch. In another example, the adjusting means may be an adjustable light guide 18 (for example a stiffened or reinforced optical cable that can receive light from the head torch and guide it to an end of the cable that is located close to the user's eyes (as shown in FIG. 2).

Preferably, the light from the second light source is predominantly directed towards the user's face and/or eyes. This means that the majority of the light emitted by the second light source falls incident on to the user's face or eyes. Preferably, the light emitted by the second light source is received by the eyes of the user at a minimum intensity. This minimum intensity of received light allows the user's body to advantageously adjust its circadian cycle as mentioned above. Preferably the minimum intensity received by the user's eyes is 0.0003 W cm$^{-2}$. More preferably, the minimum intensity is 0.0005 W cm$^{-2}$. This more preferable intensity provides a more enhanced effect of advantageously adjusting the body's circadian cycle. The distance between the second light source and the user's eyes will be dependent on the positioning of the head torch on the user's head. Generally this distance will be around 3 cm. Thus, generally the irradiance of light emitted by the second light source may be around is 0.0003 W cm$^{-2}$ at about 3 cm from the second light source. More preferably, the irradiance of light emitted by the second light source may be around is 0.0005 W cm$^{-2}$ at about 3 cm from the second light source. The luminous flux of the light emitted to achieve these irradiances will be dependent on factors such as its directionality (i.e. how diffuse the light is). The luminous flux of light emitted by the second light source may be lower than the luminous flux of light emitted by the first light source.

Preferably, the intensity of the blue light received by the user has a maximum intensity. This maximum intensity is around 0.39 W cm$^{-2}$. Thus the maximum luminous flux emitted by the second light source may suitably be chosen such that the irradiance of the light emitted is around 0.39 W cm$^{-2}$ at 3 cm from the light source. This can help prevent damage to the eyes as prolonged exposure to high intensity light can lead to long term damage to the eyes.

Preferably, the light emitted by the second light source is substantially diffuse. By providing diffuse rather than highly directional light, the user does not feel the glare of the light or feel startled or blinded by the light. Preferably, the light emitted by the first light source is more directional than the light emitted from the second light source. In other words, the light from the second light source is more diffuse than the light emitted from the first light source. This allows the user to see the light from the first light source being reflected off objects, thus allowing the user of the head torch to see objects in low light or dark conditions. As the light from the second light source is preferably diffuse, the light emitted from the second light source can be less directional than that from the first light source. Thus the beam of light emitted by the second light source can be broader than the beam from the first light source.

The second light source may comprise a light emitting device and a diffuser that is configured to diffuse the light from the light emitting device. The diffuser may be or comprise any one or more of: frosted glass; titanium oxide; plastic diffusers: lightguides; lens; film diffuser; sheet diffuser; or a sandblasted coating. Any other suitable conventionally known diffusers may be used to diffuse the light from the light emitting device.

Diffuse light from the second light source may be provided by a light emitting device that emits light in a diffuse manner (i.e. light that is not substantially directional). For example, organic light emitting diodes (OLEDS) can emit light in a substantially diffuse manner. Nano-crystal LEDs (also known as quantum-dot LEDs) can also emit light in a substantially diffuse manner. Alternative current electroluminsent devices (also known as ACELs) can also emit light in a substantially diffuse manner. Such diffuse light sources may not require an additional diffuser (such as those described above).

Thus, preferably, the user's eyes can directly receive light from the second light source whereas the light received from the first light source will be indirectly received as this light will be reflected off objects.

In another embodiment, the light emitted from the first light source may have a spectral range that is different to that of conventional white light head torches. The white light emitted by the first light may have a reduced blue component, thus providing a warmer white light. This can help offset any visual effects or artefacts that the user may perceive due to the blue light from the second light source being received by the user's eyes.

In another embodiment, the second light source may be configured to emit light in substantially the same direction as the light from the first light source. In this configuration, the light emitted by the second light source may be received by the user's eyes via reflections off objects in front of the user. This allows the user to receive the blue light without the light being directly shone into the user's eyes. Preferably, the intensity of the blue light received by the user's eyes is above a minimum intensity threshold.

The head torch can include a photo detector which can be configured to detect the intensity of blue light received by it. The photo detector receives and measures the blue light that has been reflected off objects and can provide a measure that represents the received intensity to a control circuit. Based on the measured intensity, the control circuit can adjust the power supplied to the second light source. Preferably, the control circuit adjusts the power supplied to the second light source so that a minimum intensity is received by the photo detector. Thus, the luminous flux of the blue light can be adjusted in dependence of the distance of the object that the user is viewing. This allows the blue light received by the user to be above a minimum level. This may be the minimum level required to effectively shift the circadian cycle of the user (as detailed above).

The head torch may comprise a control circuit that controls the first and second light sources. Alternatively the first and second light source may each have their own control circuit that can independently control its respective light source. The control circuit(s) can control how much power is supplied to each of the light sources from a power source (such as a battery). The control circuit(s) may be in communication with one or more switches, which allows the user to turn the light sources on or off or allows the user to make other selections (such as selecting an luminous flux to be emitted by either light source or selecting a colour to be emitted by the first light source). The switch causes the control circuit to implement the selection made by the user. Preferably, the head torch may have two switches, a first switch to control the first light source and a second switch to control the second light source. This allows the user to select a number of modes of operations, such as white light only or blue light only or both white and blue light or any other combination. The control circuit(s) can control the amount of power supplied to each light source so that each light source can emit light at specified luminous flux.

The control circuit can gradually (or incrementally) increase the power supplied to the second light source when the user switches the second light source on. The gradual increase can occur over a specified amount of time up to a specified power level (such as a level that provides luminous flux within the range specified above). This allows the user's eyes to gradually adjust to the blue light. After a specified amount if time of supplying power at the specified power level, the control circuit may gradually decrease the amount of power supplied to the second light source to zero. This can help limit the exposure to the blue light to within safe levels and by gradually decreasing the irradiance of the blue light to zero, while the user may not notice that the blue light has been turned off automatically for their safety.

In another embodiment, the head torch may comprise a third light source that is configured to emit infrared light. Preferably the infrared light is directed towards the face, below the eyes and preferably towards the nose. This is particularly advantageous to users using the head torch in cold environments as the infrared light can help to provide a comfortable level of warmth to the face/nose. The third light source may comprise an infrared light emitting diode or any other suitable infrared source.

In another embodiment, the head torch may comprise a speaker that can be configured to randomly sound alarms. This can help to keep the user alert and awake and prevent the user from falling asleep. The head torch of this embodiment may also comprise a sensor that can detect movement when the head torch is worn on the user's head. When the head torch is switched on and in use, the sensor can be configured to send a signal to the speaker to sound an alarm when the sensor detects a predetermined lack of movement. This predetermined lack of movement may indicate that the user has fallen asleep or is about to fall asleep due to the lack of movement of the user's head. The alarm can help awaken the user.

The head torch may be mounted or worn by a user using appropriate means such as a head strap or harness or other head mounting means known in the art.

The applicant hereby discloses in isolation each individual feature described herein and any combination of two or more such features, to the extent that such features or combinations are capable of being carried out based on the present specification as a whole in light of the common general knowledge of a person skilled in the art, irrespective of whether such features or combinations of features solve any problems disclosed herein, and without limitation to the scope of the claims. The applicant indicates that aspects of the present invention may consist of any such feature or combination of features. In view of the foregoing description it will be evident to a person skilled in the art that various modifications may be made within the scope of the invention.

The invention claimed is:

1. A head-mountable portable device comprising:
a first light source configured to emit a beam of white light in a first direction that is away from a head of a user; and
a second light source configured to emit a beam of blue light in a second direction that is towards the head of the user and is different to the first direction.

2. The device according to claim 1, wherein one of the first light source is configured such that the first direction of the beam of white light is adjustable independently of the second light source, or the second light source is configured such that the second direction that the blue light is substantially emitted is adjustable independently of the first light source.

3. The device according to claim 1, wherein the second light source is configured so as to substantially emit the blue light towards a face or one or more eyes of the user, and wherein the second light source is configured so as to emit the blue light in a beam that is broader than the beam of the white light.

4. The device according to claim 1, wherein a light emission spectrum of the second light source is between 400 nm and 550 nm.

5. The device according to claim 1, wherein the first light source is configured to emit light at a first luminous flux and the second light source is configured to emit light at a second luminous flux that is lower than the first luminous flux.

6. The device according to claim 1, wherein an irradiance of the blue light emitted by the second light source is 0.0003 W cm$^{-2}$ at about 3 cm from the second light source.

7. The device according to claim 1, wherein the second light source further comprises a diffuser.

8. The device according to claim 7, wherein the diffuser comprises an element selected from the group consisting of frosted glass, titanium oxide, plastic diffusers, lightguides, lens, film diffuser, sheet diffuser, and sandblasted coating.

9. The device according to claim 1 further comprising a control circuit configured to independently control the first and second light sources.

10. The device according to claim 9, wherein the control circuit is configured to independently supply power to the first and second light sources, respectively.

11. The device according claim 10, wherein the control circuit is further configured to incrementally increase the power supply to the second light source over a predetermined amount of time from a first power level to a second power level, wherein the second power level causes the second light source to emit the blue light at a predetermined luminous flux.

12. The device according to claim 11, wherein the control circuit is further configured to incrementally decrease the power supply to the second light source over a second predetermined amount of time from the second power level to the first power level.

13. The device according to claim 12, wherein the first power level is substantially zero or at a power level so as to not cause any substantial emission of the blue light from the second light source.

14. The device according to claim 13 further comprising a detector configured to measure an intensity of the blue light, wherein the control circuit is further configured to adjust the power supplied to the second light source such that the power supplied is dependent on said measured intensity.

15. The device according to claim 14, wherein the power supplied is dependent on a threshold intensity, and wherein the control circuit is configured to increase the power supplied to the second light source if the said measured intensity is lower than the threshold intensity.

16. The device according to claim 15, wherein the control circuit is configured to decrease the power supplied to the second light source if the said measured intensity is higher than the threshold intensity.

17. A method of using a head-mountable portable device in stimulation for a human user, the method comprising the steps of:
 a) providing a head-mountable portable device comprising: a first light source configured to emit a beam of white light in a first direction; and a second light source configured to emit a beam of blue light in a second direction that is different to the first direction;
 b) supplying the blue light to at least one eye of a user wearing the device; and
 c) controlling the first and second light sources independently by way of a control circuit.

* * * * *